United States Patent [19]
Heflin et al.

[11] Patent Number: 5,478,331
[45] Date of Patent: Dec. 26, 1995

[54] MULTI-FUNCTION PROXIMAL END ADAPTER FOR CATHETER

[75] Inventors: Ernest W. Heflin, Mountain View; Enrique J. Klein; Aaron V. Kaplan, both of Los Altos, all of Calif.

[73] Assignee: Localmed, Inc., Palo Alto, Calif.

[21] Appl. No.: 241,104

[22] Filed: May 11, 1994

[51] Int. Cl.⁶ .................. A61M 25/00; A61M 5/178; A61M 31/00
[52] U.S. Cl. .................. 604/283; 604/165; 604/53
[58] Field of Search .................. 604/53, 165, 167, 604/256, 283, 284

[56] References Cited

U.S. PATENT DOCUMENTS

| | | | |
|---|---|---|---|
| 4,311,137 | 1/1982 | Gerard | 604/284 |
| 4,886,507 | 12/1989 | Patton et al. | 604/284 |
| 5,129,887 | 7/1992 | Euteneuer et al. | 604/283 |
| 5,176,637 | 1/1993 | Sagae | 604/283 |
| 5,282,790 | 2/1994 | Clement | 604/167 |
| 5,352,215 | 10/1994 | Thome et al. | 604/284 |

FOREIGN PATENT DOCUMENTS 9112840  9/1991  WIPO .................. 604/284

OTHER PUBLICATIONS

Cook Incorporated Infusion Therapy Product Literature Copyright 1991.
Medex Product Literature for Tuohy-Borst Adaptor.

Primary Examiner—C. Fred Rosenbhaum
Assistant Examiner—Frank Wilkens, III
Attorney, Agent, or Firm—Townsend and Townsend and Crew

[57] ABSTRACT

A multi-function proximal end adapter (70, 86, 100) for a catheter (22) includes a hollow body (6) defining an axial lumen (8) extending between its proximal and distal ends (12, 10). An annular radially compressible seal (48) is positioned within the body along the axial lumen. A seal driver (58) is threadably mounted to the body and has a hollow extension (60) with a distal end adapted to axially compress the seal causing a radially inward deflection of the seal when the seal driver is threaded onto the body thereby providing a good seal against and securement for an object (such as a catheter or guide wire) passing through the axial lumen of the body. At least a portion of the proximal end of the axial lumen is defined by an internal tapered surface (36) sized to matingly and sealingly engage an external tapered surface (44) of a Luer lock connector (40) after the seal driver has been removed from the proximal end of the body.

19 Claims, 5 Drawing Sheets

MULTI-FUNCTION PROXIMAL END ADAPTER FOR CATHETER

BACKGROUND OF THE INVENTION

This invention relates generally to catheters and more specifically to the proximal end adapter of intravascular catheters with large central lumens which can be utilized for the infusion and withdrawal of fluids or as conduits for the introduction of devices (e.g. other catheters or guide wires). The nature of such a catheter requires that the proximal end adapter provide for dual functions: First, to allow for the connection of tubing for the infusion of solution(s) into the vessel at or near arterial pressures. Typically, Luer locks have been utilized for this singular purpose. The second function is to allow for the introduction of devices such as dilatation catheters or guide wires which are of varying diameters. To fulfill this function the proximal end adapter must be able to adjust to the diameter of the device being introduced. Also during introduction, the proximal end adapter must provide for easy slidability. After the device has been positioned, the proximal end adapter must provide an anchoring mechanism to maintain the relative position of the outer catheter with the inner smaller device. Furthermore, an adequate seal must be maintained, without damaging the shaft of the inner device, to prevent excessive loss of blood. Presently this has been accomplished with Touhy-Borst style connectors.

At present such dual function catheters are fitted with a female locking Luer lock at the proximal end adapter. Normally, when using a dual function catheter there are two options available. First is to connect a combination "Y" connector leaving a female locking Luer lock connector on one arm and a Touhy-Borst connector on the second arm. The "Y" connector is then attached to the combination catheter via its male Luer lock connector at the distal end of the "Y" connector. Infusion tubing can then be connected to the "Y" connector arm with the female Luer lock connector. The second approach is to attach a Touhy-Borst connector directly to the proximal end adapter of the intravascular catheter during device introduction. During infusion, the Touhy-Borst connector is removed and the tubing is connected directly to the proximal end adapter via the Luer lock connector. Both strategies are cumbersome.

Thus it would be desirable to provide a single proximal end adapter which would allow alternatively for the connection of infusion tubing as well as for the introduction of other devices.

SUMMARY OF THE INVENTION

The present invention is directed to a multi-functional proximal end adapter for a catheter which provides the positioning and sealing effectiveness of a Touhy-Borst-type connector, when used with devices such as catheters and guide wires, while also permitting coupling to Luer lock-type connector without an increase in length of the adapter. The invention thus combines the advantages and features of Touhy-Borst connectors with the advantages and features of Luer locks in a single, compact proximal end adapter.

The proximal end adapter includes a hollow body defining an axial lumen extending between its proximal and distal ends. An annular, radially inwardly compressible seal is positioned within the body along the axial lumen. A seal driver is threadably mounted to the body and has a hollow extension with a distal end adapted to axially compress the seal when the seal driver is threaded onto the body thereby also urging the seal to compress radially inward providing a good seal against and securement for an object passing through the axial lumen of the body. At least a portion of the proximal end of the axial lumen is defined by an internal tapered surface sized to matingly and sealingly engage an external tapered surface of a Luer lock connector after the seal driver has been removed from the proximal end of the body.

One of the primary advantages of the invention is that it eliminates the need for a separate connector to provide both Touhy-Borst and Luer lock connectors for the same arm of a catheter proximal end adapter. This significantly reduces the overall length of the adapter. Incorporating both type connectors into one adapter also reduces the cost associated with stocking additional components and the need to mount additional connectors to the adapter during a procedure. The invention also eliminates the more cumbersome technique associated with using a Luer lock on one arm of a conventional "Y" connector and a Touhy-Borst connector on the other arm of the "Y" connector.

Other features and advantages will appear from the following description in which the preferred embodiment has been set forth in detail in conjunction with the accompanying drawings.

DESCRIPTION OF THE PREFERRED EMBODIMENTS

Figure 1:
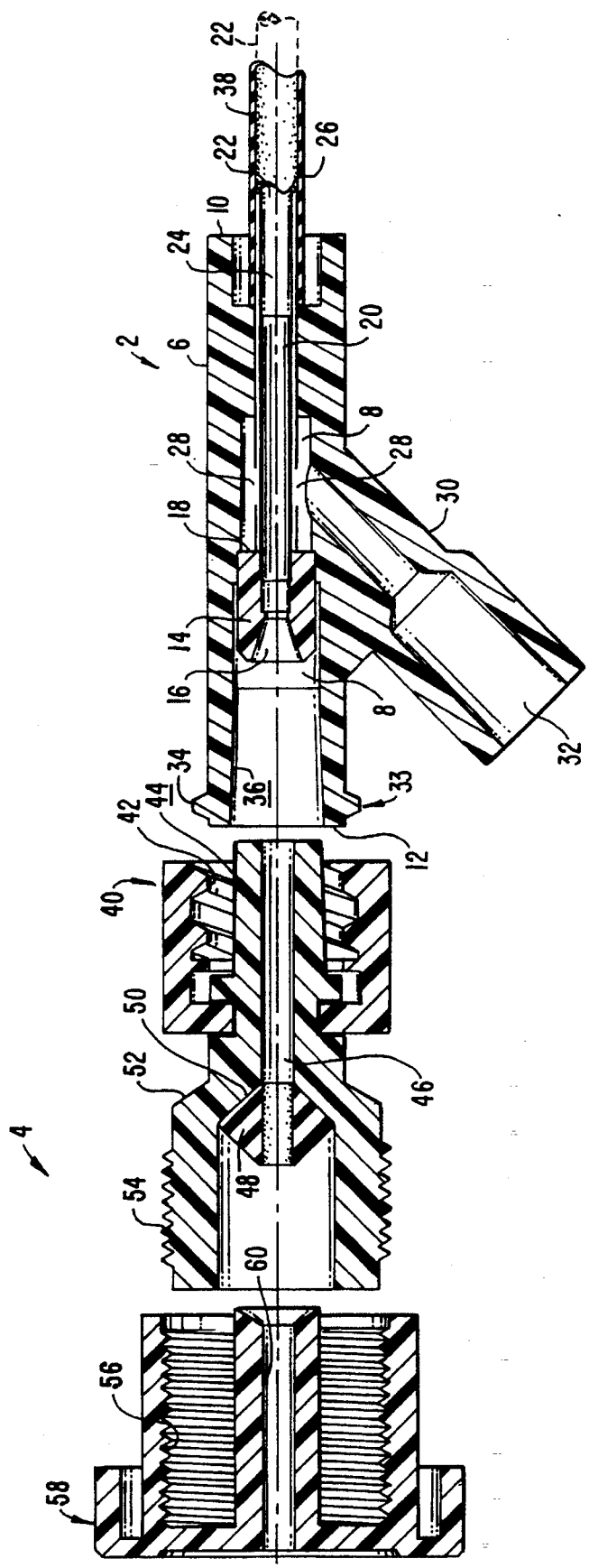
FIG. 1 is a side cross-sectional view of a prior art dual arm proximal end fitting having a female infusion port and a female Luer lock end, the fitting used with a hollow catheter sleeve and a separate Touhy-Borst connector.

The description of the invention will first involve description of a dual arm proximal end fitting shown in FIG. 1 which is not made according to the invention. It is being described to better illustrate the difference between an adapter made according to the invention, see FIGS. 2–4, and a similar fitting not made according to the invention, see FIG. 1.

FIG. 1 illustrates a catheter proximal end fitting 2 in an exploded cross-sectional relationship with a separate conventional Touhy-Borst connector 4. Fitting 2 includes a body 6 defining an axial lumen 8 extending from the distal end 10 of body 6 to the proximal end 12 of body 6. Body 6 includes an annular body fitting 14 fixed within central lumen 8. Body fitting 14 has a central passageway 16 coaxial with central lumen 8. The distal end 18 of fitting 14 supports and secures the proximal end of a support tube 20 within central lumen 8. Support tube 20 is used to mount a catheter sleeve 22 to fitting 2.

Catheter sleeve 22 defines a main lumen 24 and one or more secondary lumens 26, two being shown in FIG. 1. Catheter sleeves are shown in U.S. patent application No. 08/047,737 filed Apr. 15, 1993, now U.S. Pat. No. issued Aug. 9, 1994, for Intravascular Catheter with Infusion Array, the disclosure of which is incorporated by reference. Other catheter sleeves are shown in U.S. patent application No. filed Apr. 1, 1994, for Method and Apparatus for Sequentially Performing Multiple Intraluminal Procedures, the disclosure of which is incorporated by reference. Secondary lumens 26 have entrance ports 28 which open into axial lumen 8 adjacent a side branch 30 of body 6. Side branch 30 has an infusion side port 32 configured to accept a Luer lock. Extensions, or other types of connectors, could be used as well. Accordingly, entrance ports 28 of secondary lumens 26 are fluidly coupled to a source of fluid connected to side port 32. Similarly, proximal end 12 of body 6 incorporates a female Luer lock 33 including external threads 34 and an internal tapered surface 36. A strain relief 38 is mounted over the proximal end of catheter sleeve 22.

Touhy-Borst connector 4 includes a conventional male Luer lock 40 having internal threads 42 and an external tapered surface 44 configured for mating engagement with threads 34 and surface 36. Touhy-Borst connector 4 defines a central bore 46 which houses an annular elastomeric member 48 adjacent a shoulder 50 of the body 52 of connector 4. Body 52 has fine pitched external threads 54 formed at its proximal end which engage internal threads 56 formed on a Touhy-Borst seal driver 58. Touhy-Borst seal driver 58 includes a hollow extension 60 sized to engage and axially compress annular elastomeric member 48. Doing so causes elastomeric member 48 to deform radially inwardly onto a device, such as a catheter or a guide wire, passing through the combination of fitting 2 and connector 4. The elastomeric member not only secures the device in position and provides a good seal to help prevent, for example, the excessive loss of blood during vascular procedures, but does so with no damage to the device over a range of device diameters.

At certain times it is desired to remove the device from the combination of fitting 2 and connector 4. After this is done it is often desired to proceed with a procedure which requires mounting a Luer lock to proximal end 12 of body 6 of fitting 2. To do so, Touhy-Borst connector 4 is removed from body 6 and then the replacement Luer lock, such as one carried by a syringe as suggested in FIG. 2A, is mounted to proximal end 12. At this point the supplemental procedure, such as flushing using a syringe, can be carried out.

Figure 2:
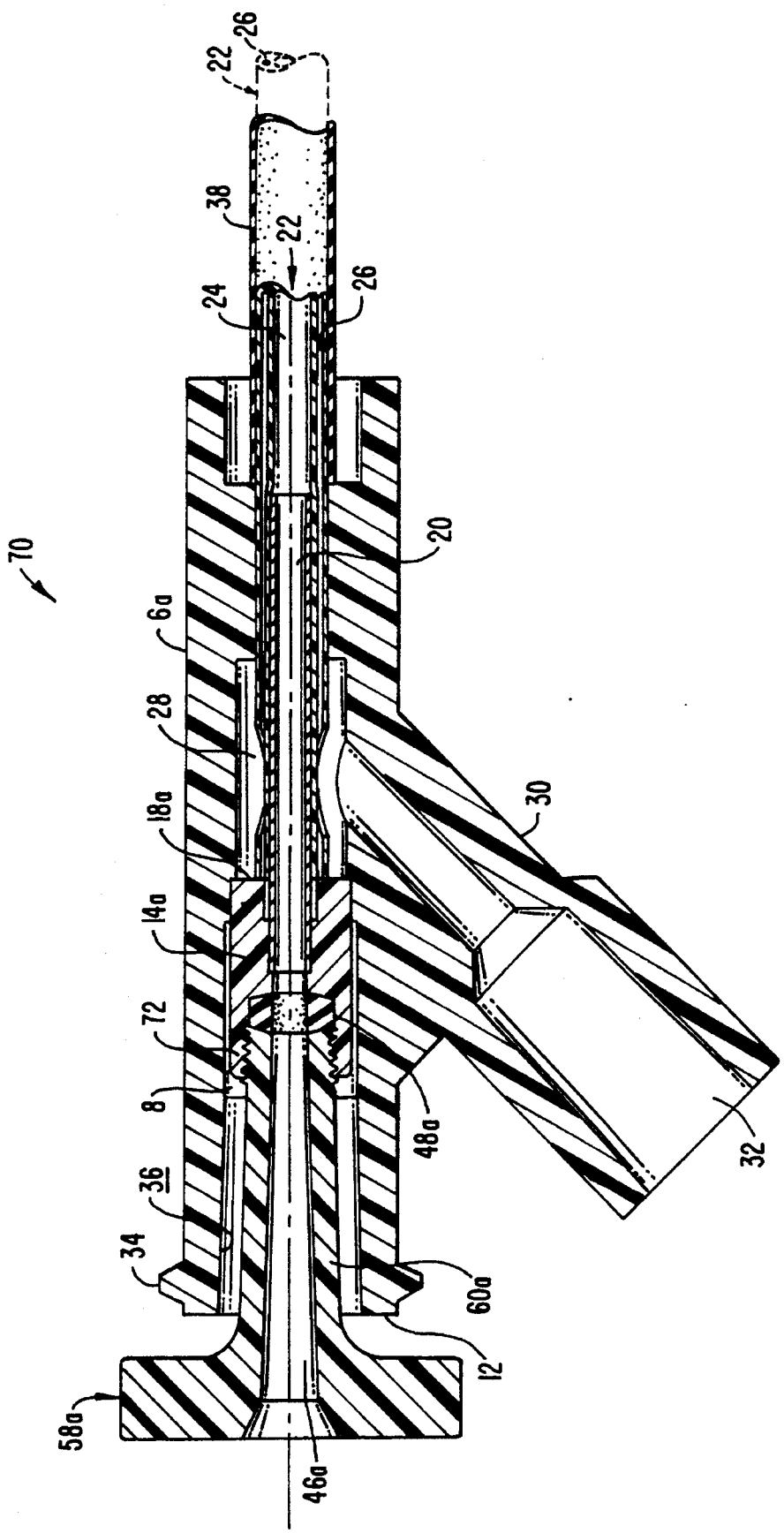
FIG. 2 is a side cross-sectional view of a first embodiment of a multi-function proximal end adapter for a catheter made according to the invention, the adapter shown connected to a catheter sleeve.
Figure 2A:
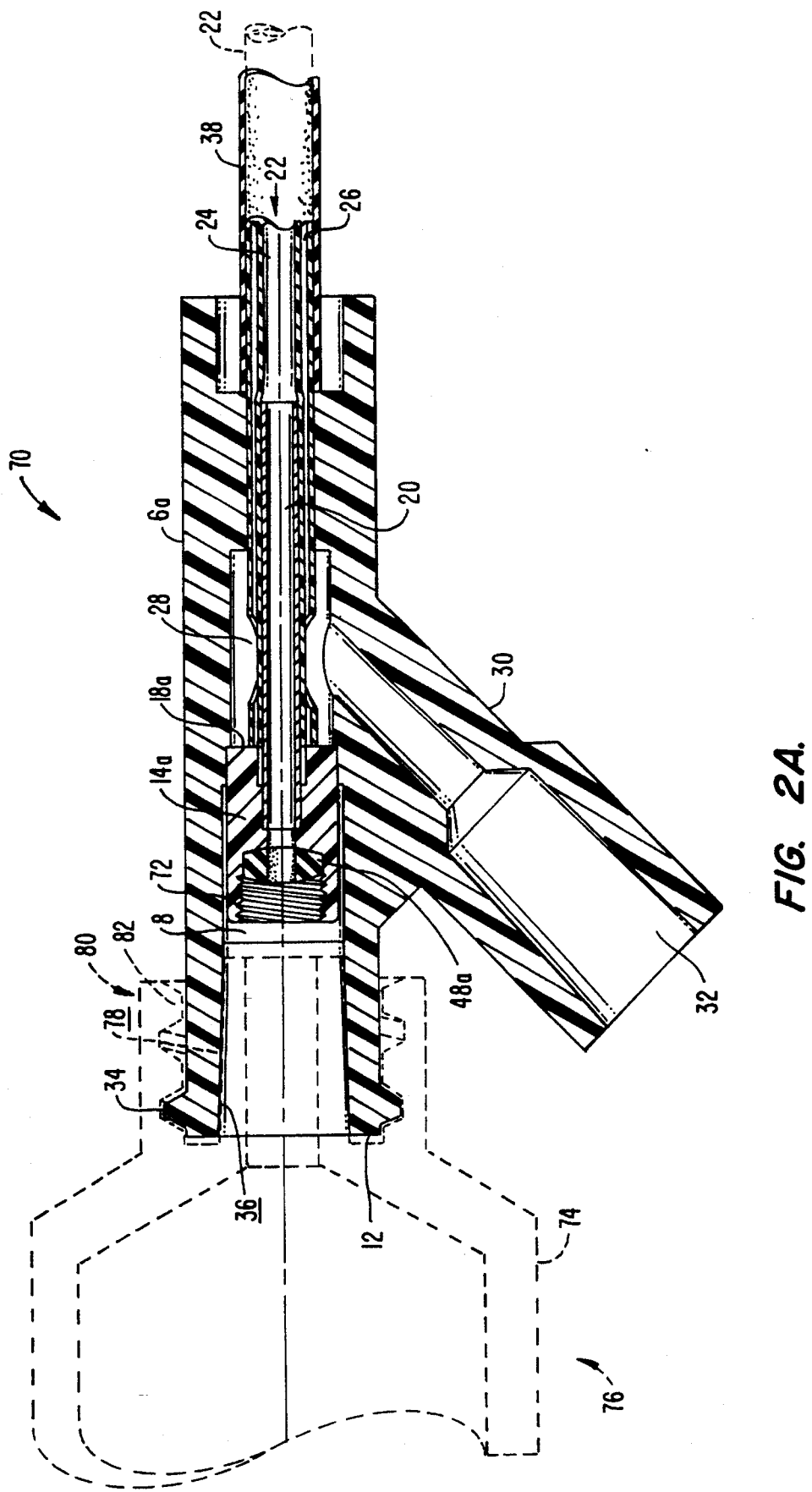
FIG. 2A illustrates the adapter of FIG. 2 with the seal driver removed and a Luer lock of a syringe, shown in dashed lines, mounted to the proximal end of the adapter body.

Referring now to FIG. 2, a multi-function proximal end adapter 70 made according to the invention is shown. As can be seen by comparing FIGS. 1 and 2, many components of adapter 70 are the same as or similar to those of FIG. 1. Those identical or similar components are identified with corresponding reference numerals and thus will not be described again. The primary difference between fitting 2 and adapter 70 is that body fitting 14a of adapter 70 is modified to receive an annular elastomeric member 48a and the threaded end 72 of hollow extension 60a of seal driver 58a. Therefore, a separate Touhy-Borst connector, as needed with fitting 2, is not needed with adapter 70. A device, such as a catheter or guide wire, passing through central bore 46a of seal driver 58a and main lumen 24 of catheter sleeve 22 can be sealed and secured in position by rotating sleeve driver 58a relative to body 6a. The threads at threaded end 72 are relatively fine-pitched threads to provide the appropriate amount of sensitivity and adjustment as is found with threads 54, 56 of conventional Touhy-Borst connector 4.

When it is desired to mount a Luer lock connector to proximal end 12, seal driver 58a is unthreaded from body fitting 14a to expose proximal end 12. FIG. 2A illustrates the distal end 74 of a syringe 76 mounted to proximal end 12 of body 6a with internal tapered surface 36a in mating engagement with external tapered surface 78 of Luer lock 80 of syringe 76. Syringe 76 is maintained in place by the engagement of internal threads 82 of Luer lock 80 with external threads 34 at proximal end 6. The appropriate procedure using syringe 76 can then be carried out.

Figure 3:
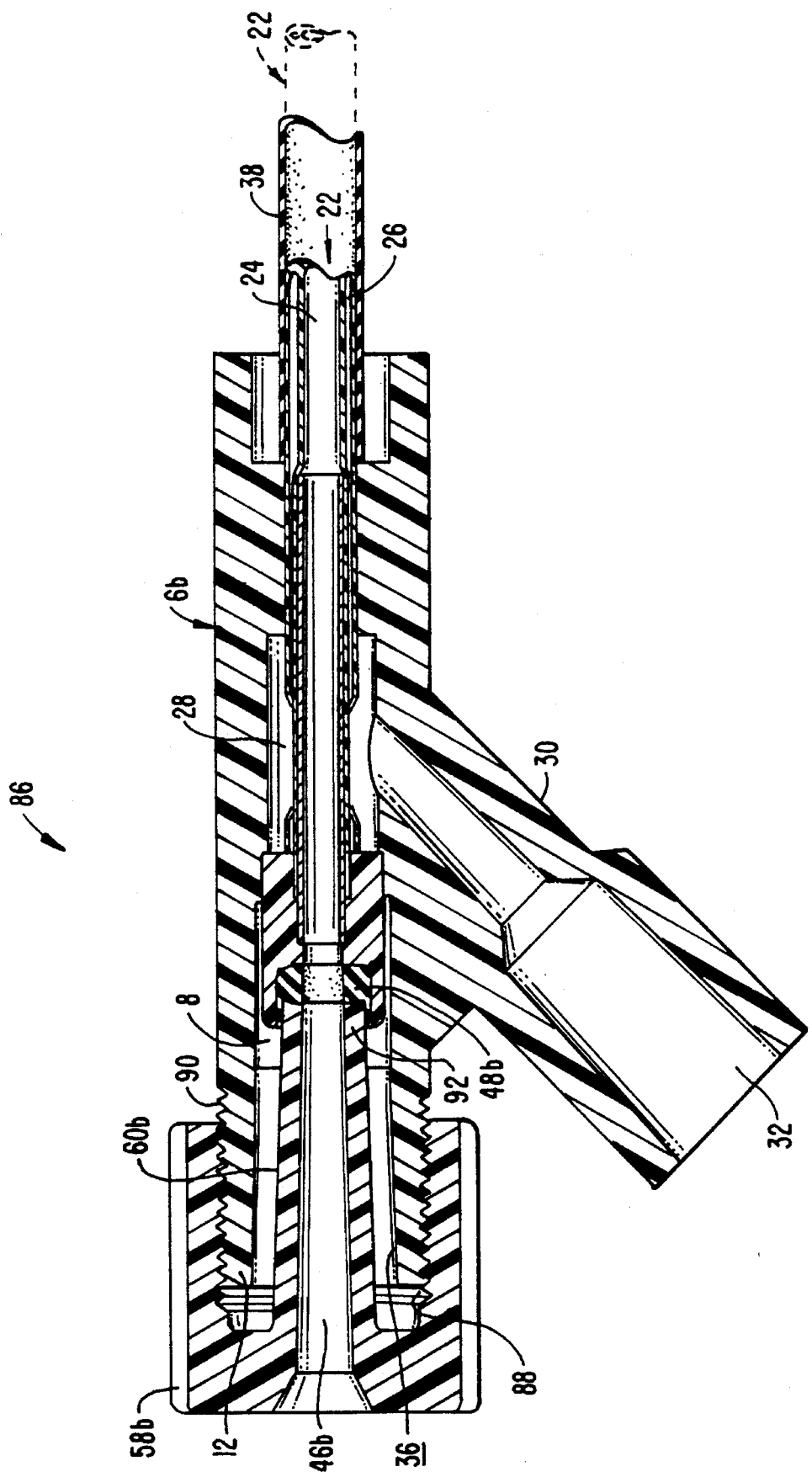
FIG. 3 is a view similar to that of FIG. 2 of a second embodiment of the invention in which the seal driver has internal threads which engage external threads formed on the body.

FIG. 3 illustrates a second embodiment of the invention in which an adapter 86 is shown with like reference numerals referring to like components of the adapter 70 of FIG. 2. Seal driver 58b has a relatively fine-pitched internal thread 88 which engages an external thread 90 formed at the proximal end 12 of body 6b. As with adapter 70 of FIG. 2, the distal end 92 of hollow extension 60b axially compresses and thus radially deforms elastomeric member 48b to provide the necessary securing and sealing of the device passing through adapter 86. To mount a Luer lock connector onto proximal end 12 of body 6b, the user unthreads seal driver 58b from the body and then inserts the external tapered surface of a Luer lock connector, such as surface 78 of Luer lock 80 of syringe 76 shown in FIG. 2A, into axial lumen 8. However, since threads 90 are not adapted for engagement with the rapidly advancing, double entry threads used on Luer locks, the engagement of Luer lock 80 with end 12 of body 6 is through a simple friction fit between surfaces 36b and 78. Accordingly, with adapter 86, user needs to ensure that the friction fit is maintained between the adapter 86 and the syringe or other Luer lock-coupled unit to ensure that the two do not disengage during the procedure. This should not be a problem where the procedure is a relatively short term procedure, such as flushing main lumen 24 of the catheter sleeve 22 with the contents of syringe 76.

Figure 4:
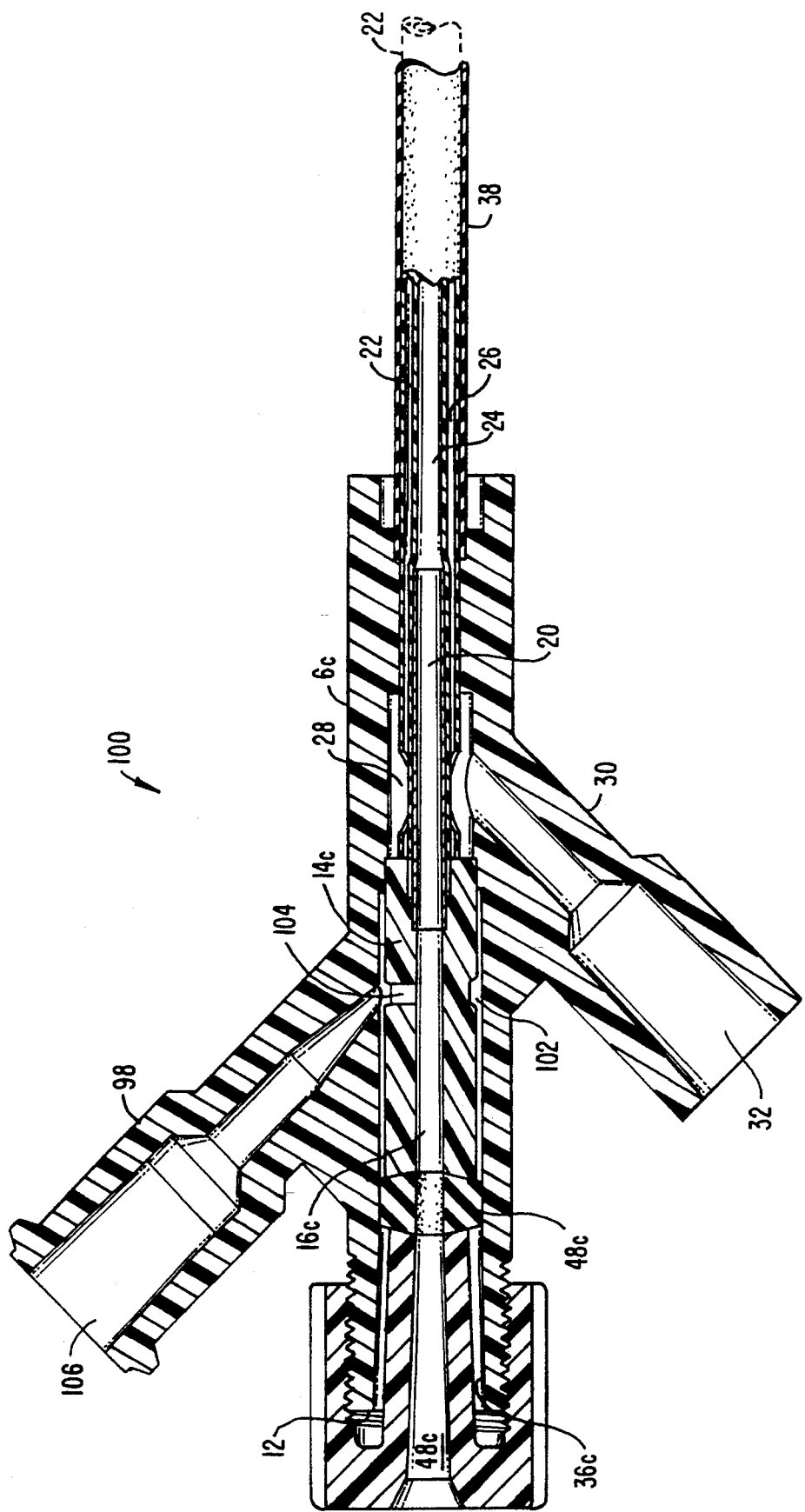
FIG. 4 is a view similar to that of FIG. 3 but of a triple arm embodiment of the invention having a second side branch fluidly coupled to the main lumen of the catheter sleeve.

FIG. 4 illustrates a further embodiment of the invention similar to that of FIG. 3 but including a second side branch 98. Side branch 98 of adapter 100 is fluidly coupled to an annular groove 102 formed in body fitting 14c. Body fitting 14c also has a radially extending port 104 fluidly coupling groove 102 and central passageway 16c so as to fluidly couple second side port 106 to main lumen 24 of catheter sleeve 22. The operation of adapter 100 is similar to that of adapter 86. However, with adapter 100, flushing of main lumen 24 can at times take place while a device, such as a guide wire, remains within the main lumen and is sealed by elastomeric member 48c. However, adapter 100 also includes tapered surface 36c which permits a Luer lock connector, such as from syringe 76, to be mounted to proximal end 12 of body 6c.

Reference has been made to threads and tapered surfaces suitable for use with Luer lock type connectors. Generally, Luer locks have a 6% included angle taper as fully characterized in publication ISO 594/1, First Edition, 1986-06-15 and made part of this application by reference. Luer lock connectors have a double start, right-hand thread described in publication ISO 594-2, First Edition, 1991-05-01 made part of this application by reference.

Body 6 may be of metal or a variety of biocompatible rigid plastics, such as ABS, acetal or polycarbonate. Annular elastomeric mender 48 can be made from natural or synthetic rubber, in particular silicone rubber.

Other modifications and variations can be made to the disclosed embodiments without departing from the subject of the invention as defined in the following claims. For example, in FIG. 2 relatively course external threads 34 could be made to extend a distance along body 70 and have relatively fine external threads 90 formed into the outer surfaces of the relatively course threads 34. This would permit an external device, such as syringe 76, to be secured to proximal end 12 of the body of an adapter similar to that of FIG. 2 using Luer lock type threads while also using a seal driver similar to seal driver 58b of FIG. 3. Seal driver 58b and body 6b could be modified to replace relatively fine threads 88, 90 with conventional Luer lock threads. In the preferred embodiment the radial deformation of elastomeric member 48 is created by the axial compression of the member. However, this radial deformation could take place in other ways, such as by applying an inwardly directed force on elastomeric member 48, such as through the use of a collet.

What is claimed is:

1. A multi-function proximal end adapter for a catheter comprising:

a one-piece body, having proximal and distal ends, defining an axial lumen extending between the proximal and distal ends;

a catheter mounting element for mounting a catheter directly to the body;

a radially compressible seal, having a central bore, positioned within the body along the axial lumen at a distance from the proximal end;

compression means for causing the radially compressible seal to compress inwardly; and at least part of a proximal end portion of the axial lumen proximal of the seal being defined by an internal tapered surface sized to matingly and sealingly engage an external tapered surface of a Luer lock connector.

2. A combination of the adapter of claim 1 and a hollow catheter, wherein the catheter mounting element is adapted to connect the body to the hollow catheter so the hollow catheter extends from the distal end of the body.

3. The combination of claim 2 wherein the hollow catheter defines a main, axially extending lumen and at least one secondary, radially offset, axially extending lumen.

4. The combination of claim 3 wherein the secondary lumen includes an entrance port opening into a portion of the axial lumen of the body.

5. The combination of claim 4 wherein the body includes a side branch having a side port fluidly connected to the entrance port though the portion of the axial lumen, and further comprising means for sealing said portion of the axial lumen from the axial lumen proximal and distal of said portion.

6. The adapter of claim 1 wherein the body includes a side branch having a side port fluidly connected to a portion of the axial lumen at a position distal of the seal.

7. The adapter of claim 1 wherein the radially compressible seal includes an elastomeric annular member.

8. The adapter of claim 1 wherein the compression means includes:

a seal driver, having a first thread;

the body having a second thread engageable with the first thread; and the seal driver including a hollow extension having a distal end adapted to axially compress the seal when the first thread threadably engages the second thread.

9. The adapter of claim 8 wherein the second thread is an internal thread.

10. The adapter of claim 9 wherein the body further comprises an annular body fitting coaxially housed within the axial lumen, the second thread being part of the annular body fitting.

11. The adapter of claim 9 wherein the second thread is adjacent the seal and the first thread is adjacent the distal end of the extension of the seal driver.

12. The adapter of 8 wherein the second thread is an external thread.

13. A combination multi-function proximal end adapter and a hollow catheter sleeve comprising:

a one-piece body, having proximal and distal ends, defining an axial lumen extending between the proximal and distal ends;

a hollow catheter secured within and extending from the axial lumen at the distal end of the body, the hollow catheter defining a main, axially extending lumen and at least one secondary, radially offset, axially extending lumen, the secondary lumen including an entrance port opening into a first portion of the axial lumen of the body;

the body further comprising a side branch having a side port fluidly connected to the entrance port though a second portion of the axial lumen;

a radially compressible seal, having a central bore, positioned within the body along the axial lumen at a distance from the proximal end;

compression means for causing the radially compressible seal to compress inwardly, the compression means comprising:

a seal driver, having a first thread;

the body having a second thread engageable with the first thread; and the seal driver including a hollow extension having a distal end adapted to axially compress, thereby radially inwardly deflecting, the seal when the first thread threadably engages the second thread; and at least part of a proximal end portion of the axial lumen proximal of the seal being defined by an internal tapered surface sized to matingly and sealingly engage an external tapered surface of a Luer lock connector.

14. A method for use of a proximal end adapter of a catheter, the adapter having a one-piece body with an axial lumen extending between the proximal and distal ends of the body, the axial lumen defined in part by an internal tapered surface located towards the proximal end, comprising the following steps:

mounting a first connector, having an external tapered surface, to the proximal end of the one-piece body with the external tapered surface matingly engaging the internal tapered surface to provide a fluid seal therebetween;

conducting a first procedure using the first connector;

removing the first connector from the proximal end of the body;

threadably mounting a second connector to the proximal end of the body; and threadably adjusting the engagement of the second connector on the proximal end of the body thereby causing a resilient annular seal housed within the axial lumen to deflect radially inwardly and sealingly engage a device passing through the axial lumen.

15. The method of claim 14 wherein the mounting step is carried out with a 6% included angle taper to the external tapered surface.

16. The method of claim 14 wherein the mounting step includes the step of threadably securing the first connector to the body.

17. The method of claim 14 wherein the threadably mounting step is carried out using a one-piece second connector.

18. The method of claim 14 wherein the threadably adjusting step is carried out by axially compressing the annular seal causing the annular seal to deflect radially inwardly.

19. The method of claim 14 wherein the threadably mounting step is carried out using an externally threaded second connector and threadably coupling said second connector to internal threads carried by the body.

* * * * *